United States Patent
Govari

(10) Patent No.: US 12,426,944 B2
(45) Date of Patent: Sep. 30, 2025

(54) AUTOMATICALLY PERFORMING IRREVERSIBLE ELECTROPORATION ABLATION DURING HEART REFRACTORY PERIOD

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 245 days.

(21) Appl. No.: 16/940,767

(22) Filed: Jul. 28, 2020

(65) Prior Publication Data

US 2022/0031385 A1 Feb. 3, 2022

(51) Int. Cl.
| | | |
|---|---|---|
| A61B 18/14 | (2006.01) | |
| A61B 5/318 | (2021.01) | |
| A61B 5/36 | (2021.01) | |
| A61B 17/00 | (2006.01) | |
| A61B 18/00 | (2006.01) | |
| A61B 18/12 | (2006.01) | |

(52) U.S. Cl.
CPC .............. *A61B 18/1492* (2013.01); *A61B 2017/00044* (2013.01); *A61B 2017/00132* (2013.01); *A61B 2018/00357* (2013.01); *A61B 2018/00577* (2013.01); *A61B 2018/00613* (2013.01); *A61B 2018/00839* (2013.01); *A61B 2018/126* (2013.01)

(58) Field of Classification Search
CPC ...... A61B 18/1492; A61B 2017/00044; A61B 2017/00132; A61B 2018/00357; A61B 2018/00577; A61B 2018/00613; A61B 2018/00839

See application file for complete search history.

(56) References Cited

U.S. PATENT DOCUMENTS

| | | |
|---|---|---|
| 5,391,199 A | 2/1995 | Ben Haim |
| 6,239,724 B1 | 5/2001 | Doron |
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben Haim |
| 8,048,067 B2 | 11/2011 | Davalos |
| 8,221,411 B2 | 7/2012 | Francischelli |

(Continued)

FOREIGN PATENT DOCUMENTS

| | | |
|---|---|---|
| RU | 2413551 C2 | 3/2011 |
| WO | WO1996005768 A1 | 2/1996 |
| WO | WO2017024123 A1 | 2/2017 |

OTHER PUBLICATIONS

Claudio Bertacchini, M.S., Design of an Irreversible Electroporation System for Clinical Use, Technology in Cancer Research and Treatment, vol. 6, No. 4, Aug. 2007, c. 313-320.

(Continued)

*Primary Examiner* — Joseph A Stoklosa
*Assistant Examiner* — Annie L Shoulders

(57) ABSTRACT

A method includes inserting an ablation catheter into an ablation site in a patient heart. Multiple electrocardiogram (ECG) signals are acquired. A refractory period of the patient heart is detected based on the acquired ECG signals. The ablation site is ablated using the ablation catheter during the detected refractory period.

9 Claims, 2 Drawing Sheets

(56) References Cited

U.S. PATENT DOCUMENTS

| | | |
|---|---|---|
| 9,764,145 B2 | 9/2017 | Callas |
| 9,987,081 B1* | 6/2018 | Bowers .............. A61B 18/1492 |
| 10,172,673 B2* | 1/2019 | Viswanathan ......... A61N 1/056 |
| 10,271,893 B2 | 4/2019 | Stewart |
| 10,322,286 B2 | 6/2019 | Viswanathan |
| 10,342,598 B2 | 7/2019 | Long |
| 10,433,908 B2 | 10/2019 | Viswanathan |
| 10,531,914 B2* | 1/2020 | Stewart .................. A61N 1/327 |
| 10,625,080 B1* | 4/2020 | Viswanathan ......... A61B 5/347 |
| 2002/0065455 A1 | 5/2002 | Ben Haim |
| 2003/0120150 A1 | 6/2003 | Govari |
| 2004/0068178 A1 | 4/2004 | Govari |
| 2016/0051324 A1 | 2/2016 | Stewart |
| 2016/0166310 A1* | 6/2016 | Stewart .............. A61B 18/1492 |
| | | 606/34 |
| 2017/0035499 A1 | 2/2017 | Stewart et al. |
| 2019/0060632 A1 | 2/2019 | Asirvatham |
| 2019/0201688 A1 | 7/2019 | Olson |
| 2019/0336198 A1 | 11/2019 | Viswanathan et al. |
| 2021/0137384 A1* | 5/2021 | Robinson .............. A61B 5/0044 |
| 2021/0338302 A1* | 11/2021 | Paré ....................... A61B 18/00 |
| 2023/0181250 A1* | 6/2023 | Viswanathan ..... A61B 18/1492 |
| | | 606/41 |

OTHER PUBLICATIONS

Extended European Search Report received for European Application No. 21165831.5, mailed on Sep. 21, 2021, 8 pages.

* cited by examiner

AUTOMATICALLY PERFORMING IRREVERSIBLE ELECTROPORATION ABLATION DURING HEART REFRACTORY PERIOD

FIELD OF THE INVENTION

The present invention relates generally to tissue ablation, and particularly to methods and systems for improving patient safety in irreversible electroporation ablation procedures.

BACKGROUND OF THE INVENTION

Various techniques for ablating heart tissue by applying irreversible electroporation (IRE) pulses are known in the art.

For example, U.S. Pat. No. 10,531,914 describes a method for ablating tissue by applying at least one pulse train of pulsed-field energy. The method includes delivering a pulse train of energy having a predetermined frequency to cardiac tissue.

U.S. Pat. No. 10,322,286 describes a system including a pulse waveform generator and an ablation device coupled to the pulse waveform generator. The ablation device includes at least one electrode configured for ablation pulse delivery to tissue during use. The pulse waveform generator is configured to deliver voltage pulses to the ablation device in the form of a pulsed waveform.

SUMMARY OF THE INVENTION

An embodiment of the present invention that is described herein provides a method including inserting an ablation catheter into an ablation site in a patient heart. Multiple electrocardiogram (ECG) signals are acquired using the catheter. A refractory period of the patient heart is detected based on the acquired ECG signals. The ablation site is ablated using the ablation catheter during the detected refractory period.

In some embodiments, acquiring the multiple ECG signals includes acquiring at least one of (i) intra-cardiac (IC) ECG signals at the ablation site, and (ii) body-surface (BS) ECG signals. In other embodiments, detecting the refractory period includes indicating a sinus rhythm in at least one of the acquired ECG signals.

In an embodiment, ablating the ablation site includes applying one or more irreversible electroporation (IRE) pulses to tissue at the ablation site during the detected refractory period. In another embodiment, applying the one or more IRE pulses includes controlling an IRE pulse generator and applying the IRE pulses to the tissue in response to receiving at least one of the ECG signals that is indicative of the sinus rhythm.

There is additionally provided, in accordance with an embodiment of the present invention, a system including one or more electrodes and a processor. The one or more electrodes are configured to sense multiple electrocardiogram (ECG) signals of a patient heart. The processor is configured, based on the acquired ECG signals, to detect a refractory period of the patient heart, and to control ablation at an ablation site during the detected refractory period.

In some embodiments, the electrodes include: (i) at least a first electrode fitted on a catheter and configured to sense intra-cardiac (IC) ECG signals at the ablation site, and (ii) second electrodes coupled to a surface of the patient, and configured to sense body-surface (BS) ECG signals of the patient heart. In other embodiments, the processor is configured to detect the refractory period based on at least one of the ECG signals, which is indicative of a sinus rhythm pulse. In yet other embodiments, the system includes an irreversible electroporation (IRE) pulse generator, which is configured to apply IRE pulses to tissue at the ablation site during the detected refractory period.

In an embodiment, the IRE pulse generator is configured to apply one or more bipolar IRE pulses between a pair of the electrodes, which are in contact with tissue at the ablation site. In another embodiment, at least one of the one or more electrodes is fitted on a catheter and is configured to perform at least one of: (i) sensing intra-cardiac ECG signals at the ablation site, and (ii) applying one or more irreversible electroporation (IRE) pulses, to tissue at the ablation site.

There is further provided, in accordance with an embodiment of the present invention, a system including: (i) an interface, which is configured to receive multiple electrocardiogram (ECG) signals of a patient heart, and (ii) a processor, which is configured, based on the received ECG signals, to detect a refractory period of the patient heart, and to control ablation at the ablation site during the detected refractory period.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
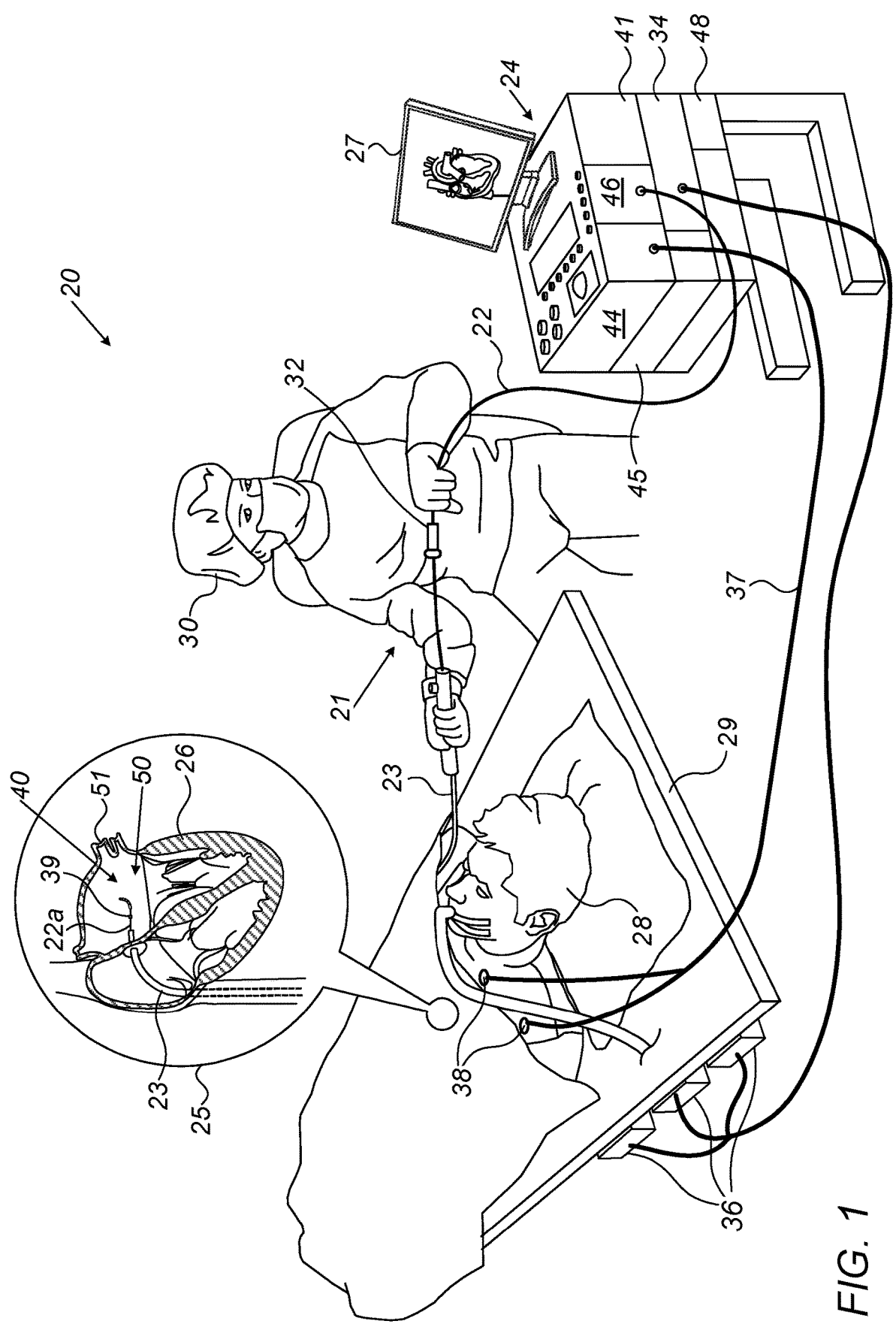
FIG. 1 is a schematic, pictorial illustration of a catheter-based position-tracking and irreversible electroporation (IRE) ablation system, in accordance with an exemplary embodiment of the present invention.

Irreversible electroporation (IRE) may be used, for example, for treating arrhythmia by ablating tissue cells using high voltage applied pulses. Cellular destruction occurs when the transmembrane potential exceeds a threshold, leading to cell death and formation of a lesion. In IRE-based ablation procedures, high-voltage bipolar electrical pulses are applied, for example, to a pair of electrodes in contact with tissue to be ablated, so as to form a lesion between the electrodes, and thereby to treat arrhythmia in a patient heart.

The rhythm of patient heart is determined, inter alia, by electrical activation pulses initiated by a sinus node of the heart. Thus, applying IRE pulses and activation pulses at the same time may interfere with the heart rhythm and therefore, be hazardous to the patient.

Embodiments of the present invention that are described hereinbelow provide improved techniques for applying one or more IRE pulses during a refractory period between electrical activation pulses of the sinus node.

In some embodiments, a physician inserts an ablation catheter into an ablation site having tissue intended to be ablated in a patient heart. The ablation catheter comprises at least a pair of electrodes, which are in contact with heart tissue at the ablation site.

The pair of electrodes (also referred to herein as first electrodes) are configured to acquire intra-cardiac (IC) electrocardiogram (ECG) signals at the ablation site of the patient heart, and also, to apply bipolar IRE pulses to the heart tissue located between the two electrodes of the pair.

In some embodiments, a second set of multiple electrodes are coupled, for example, to the patient skin, so as to acquire body-surface (BS) ECG signals from the patient heart.

In some embodiments, a processor is configured to receive both the IC and BS ECG signals, and to check whether one or more of the acquired ECG signals is in the rhythm of the sinus node. In response to identifying one or more IC and/or BS ECG signals in the rhythm of the sinus node, the processor is configured to detect a refractory period of the patient heart, and to control an IRE pulse generator (IPG) to apply one or more IRE pulse (via at least a pair of the first electrodes) to the ablation site during the detected refractory period. Note that the entire process described above is carried out automatically, e.g., without intervention of the physician, however, the physician may have the means to intervene, and if needed, to adjust or abort the IRE ablation procedure.

The disclosed techniques improve the quality and safety of tissue ablation, by preventing events of applying IRE pulses to tissue at the same time when the sinus node applies the activation pulses, and by ensuring that IRE pulses are applied to tissue of the ablation site during refractory periods. Moreover, the disclosed techniques take away from the physician some of the burden associated with performing the IRE procedure, and allow him/her to monitor the quality of the IRE procedure.

System Description

FIG. 1 is a schematic, pictorial illustration of a catheter-based position-tracking and irreversible electroporation (IRE) ablation system 20, in accordance with an embodiment of the present invention.

Reference is now made to an inset 25. In some embodiments, system 20 comprises a deflectable tip section 40 that is fitted at a distal end 22a of a shaft 22 of a catheter 21 with deflectable tip section 40 comprising multiple electrodes 50.

In the embodiment described herein, electrodes 50 are configured to sense intra-cardiac (IC) electrocardiogram (ECG) signals, and may additionally be used for IRE ablation of tissue of left atrium of a heart 26, such as IRE ablation of an ostium 51 of a pulmonary vein (PV) in heart 26. Note that the techniques disclosed herein are applicable, mutatis mutandis, to other sections (e.g., atrium or ventricle) of heart 26, and to other organs of a patient 28.

Reference is now made back to the general view of FIG. 1. In some embodiments, the proximal end of catheter 21 is connected to a control console 24 (also referred to herein as a console 24, for brevity) comprising an ablative power source, in the present example an IRE pulse generator (IPG) 45, which is configured to deliver peak power in the range of tens of kilowatts (kWs). Console 24 comprises a switching box 46, which is configured to switch the power applied by IPG 45 to one or more selected pairs of electrodes 50. A sequenced IRE ablation protocol may be stored in a memory 48 of console 24.

In some embodiments, a physician 30 inserts distal end 22a of shaft 22 through a sheath 23 into heart 26 of patient 28 lying on a table 29. Physician 30 navigates distal end 22a of shaft 22 to a target location in heart 26 by manipulating shaft 22 using a manipulator 32 positioned near the proximal end of catheter 21. During the insertion of distal end 22a, deflectable tip section 40 is maintained in a straightened configuration by sheath 23. By containing tip section 40 in a straightened configuration, sheath 23 also serves to minimize vascular trauma when physician 30 moves catheter 21, through the vasculature of patient 28, to the target location, such as an ablation site, in heart 26.

Once distal end 22a of shaft 22 has reached the ablation site, physician 30 retracts sheath 23 and deflects tip section 40, and further manipulates shaft 22 to place electrodes 50 disposed over tip section 40 in contact with ostium 51 at the ablation site. In the present example, the ablation site comprises one or more PVs of heart 26, but in other embodiments, physician 30 may select any other suitable ablation site.

In some embodiments, electrodes 50 are connected by wires running through shaft 22 to a processor 41, which is configured to control switching box 46 using interface circuits 44 of console 24.

As further shown in inset 25, distal end 22a comprises a position sensor 39 of a position tracking system, which is coupled to distal end 22a, e.g., at tip section 40. In the present example, position sensor 39 comprises a magnetic position sensor, but in other embodiments, any other suitable type of position sensor (e.g., other than magnetic based) may be used. During navigation of distal end 22a in heart 26, processor 41 receives signals from magnetic position sensor 39 in response to magnetic fields from external field generators 36, for example, for the purpose of measuring the position of tip section 40 in heart 26 and, optionally, for displaying the tracked position overlaid on the image of heart 26, on a display 27 of console 24. Magnetic field generators 36 are placed at known positions external to patient 28, e.g., below table 29. Console 24 also comprises a driver circuit 34, configured to drive magnetic field generators 36.

The method of position sensing using external magnetic fields is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1, whose disclosures are all incorporated herein by reference.

Typically, processor 41 of console 24 comprises a general-purpose processor of a general-purpose computer, with suitable front end and interface circuits 44 for receiving signals from catheter 21, as well as for applying ablation energy via catheter 21 in a left atrium of heart 26 and for controlling the other components of system 20. Processor 41 typically comprises a software in memory 48 of system 20, which is programmed to carry out the functions described herein. The software may be downloaded to the computer in electronic form, over a network, for example, or it may, alternatively or additionally, be provided and/or stored on non-transitory tangible media, such as magnetic, optical, or electronic memory.

Performing Irreversible Electroporation Ablation During Heart Refractory Period

Irreversible electroporation (IRE), also referred to as Pulsed Field Ablation (PFA), may be used as a minimally invasive therapeutic modality to kill tissue cells at the ablation site by applying high-voltage pulses to the tissue. In the present example, IRE pulses may be used for killing myocardium tissue cells in order to treat cardiac arrhythmia in heart 26. Cellular destruction occurs when the transmembrane potential exceeds a threshold, leading to cell death and thus the development of a tissue lesion. Therefore, of particular interest is the use of high-voltage bipolar electrical pulses, e.g., using a pair of electrodes 50 in contact with tissue at the ablation site, to generate high electric fields (e.g., above a certain threshold) to kill tissue cells located between the electrodes.

In the context of this disclosure, "bipolar" voltage pulse means a voltage pulse applied between two electrodes 50 of catheter 21 (as opposed, for example, to unipolar pulses that are applied, e.g., during a radio-frequency ablation, by a catheter electrode relative to some common ground electrode not located on the catheter).

To implement IRE ablation over a relatively large tissue region of heart 26, such as a circumference of an ostium of a pulmonary vein (PV) or any other suitable organ, it is necessary to use multiple pairs of electrodes 50 of catheter 21 having multi electrodes 50 in deflectable tip section 40. To make the generated electric field as spatially uniform as possible over a large tissue region it is best to have pairs of electrodes 50 selected with overlapping fields, or at least fields adjacent to each other. However, there is a Joule heating component that occurs with the IRE generated fields, and this heating may damage the electrodes when multiple pairs of electrodes 50 are continuously used for delivering a sequence of IRE pulses.

In an embodiment, system 20 comprises surface electrodes 38, shown in the example of FIG. 1, as attached by wires running through a cable 37 to the chest and shoulder of patient 28. In some embodiments, surface electrodes 38 are configured to sense body-surface (BS) ECG signals in response to beats of heart 26. Acquisition of BS ECG signals may be carried out using conductive pads attached to the body surface or any other suitable technique. Any pair of electrodes 38 can measure the electrical potential difference between the two corresponding locations of attachment. Such a pair forms a lead. However, "leads" can also be formed between a physical electrode and a virtual electrode, known as the Wilson's central terminal. For example, ten electrodes 38 attached to the body are used to form 12 ECG leads, with each lead measuring a specific electrical potential difference in heart 26. As shown in FIG. 1, surface electrodes 38 are attached to the chest and shoulder of patient 28, however, additional surface electrodes 38 may be attached to other organs of patient 28, such as limbs. In the context of the present disclosure and in the claims, the electrical potential difference measured between surface electrodes 38 are referred to herein as body-surface (BS) ECG signals.

In heart 26, a sinus rhythm is any cardiac rhythm in which depolarization of the cardiac muscle begins at the sinus node. The sinus rhythm is characterized by the presence of correctly oriented P waves on the ECG. Sinus rhythm is necessary, but not sufficient, for normal electrical activity within the heart. After an action potential initiates (e.g., by the sinus node), a cardiac cell of heart 26 is unable to initiate another action potential for some duration of time. This period of time is referred to herein as a refractory period, which is about 250 ms in duration and helps to protect the heart.

In some embodiments, electrodes 50 are configured to sense the aforementioned IC ECG signals, and (e.g., at the same time) surface electrodes 38 are sensing the BS ECG signals.

In some embodiments, processor 41 is configured to receive the body-surface (BS) ECG signals from surface electrodes 38, and the intra-cardiac (IC) ECG signals from electrodes 38. Processor 41 is further configured to check whether either the IC ECG signals, or the BS ECG signals are in the rhythm of the sinus node.

In some embodiments, in case none of the acquired ECG signals is in the rhythm of the sinus node, processor 41 continues to receive and analyze additional IC and BS ECG signals over time.

In some embodiments, based on the acquired BS and IC ECG signals, and in response to ECG signals that are in the rhythm of the sinus node, processor 41 is configured to detect the refractory period of heart 26. Note that for safety reasons, applying IRE pulses is allowed during the refractory period and not during the initiation of action potential.

In some embodiments, processor 41 is configured to control IPG 45 to apply one or more IRE pulses to tissue at the ablation site of heart 26, via one or more pairs of electrodes 50 selected by switching box 46. For example, physician 30 may send a command to processor 21 to activate IPG 45 (or may directly activate a controller of IPG 45), e.g., by pressing a foot pedal. Processor 41 is configured to receive the IC and BS ECG signals from electrodes 50 and 38, respectively, and to control IPG 45 to apply the IRE pulses at the detected refractory period when at least one of the IC and/or BS ECG signals indicates a sinus rhythm. In other words, when detecting the refractory period of heart 26, processor 41 controls IPG 45 to apply the IRE pulses to tissue of the ablation site of heart 26.

In some embodiments, processor 41 is configured to carry out the IRE ablation procedure automatically. In such embodiments, processor 41 is configured to control: (i) the number and quality of IC and BS ECG signals acquired from heart 26, (ii) the timing for applying the IRE pulses to tissue 9 during one or more refractory periods), and (iii) at least some parameters of the applied IRE pulses. Note that after positioning at least a pair of electrodes 50 in contact with tissue at the ablation site, physician 30 may command processor 41 to control the acquisition of the ECG signal and the applying of the IRE pulses, automatically. However, if required (e.g., in case of emergency), physician 30 may intervene in the IRE procedure, e.g., by adjusting and/or aborting the process carried out by processor 41.

Figure 2:
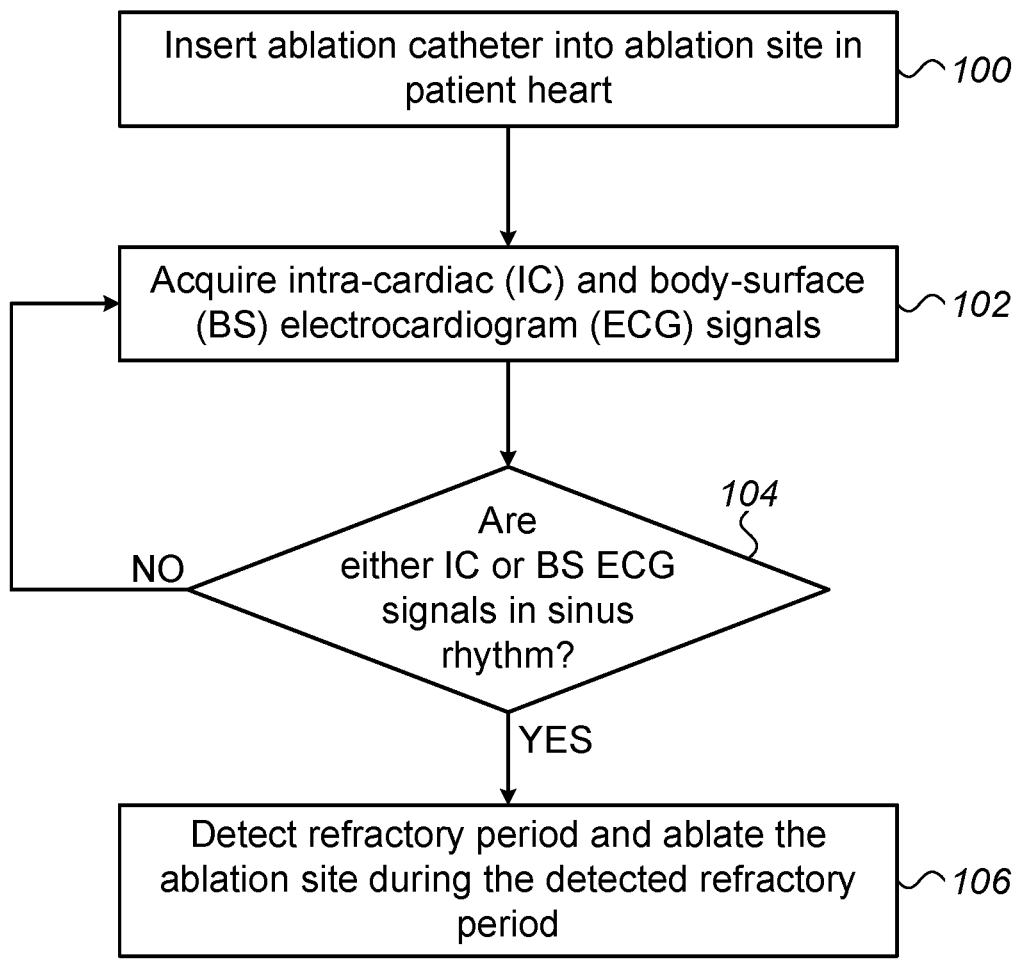
FIG. 2 is a flow chart that schematically illustrates a method for automatically performing IRE ablation during heart refractory period, in accordance with an exemplary embodiment of the present invention.

FIG. 2 is a flow chart that schematically illustrates a method for automatically performing IRE ablation during a refractory period of heart 26, in accordance with an embodiment of the present invention.

The method begins at a catheter insertion step 100, with physician inserting catheter 21, and using the position tracking system for positioning one or more pairs of electrodes 50 attached to the ablation site of heart 26, as described in FIG. 1 above.

At an ECG signal acquisition step 102, processor 41 is configured to receive intra-cardiac (IC) and body-surface (BS) ECG signals from electrodes 50 and 38, respectively, as described in FIG. 1 above.

At a sinus rhythm detection step 104, processor 41 is configured to check whether one or more IC ECG signals and/or BS ECG signals are in the rhythm of the sinus node. In case no ECG signals found in the rhythm of the sinus node, the method loops back to step 102 and processor 41 continues to check additional IC and BS ECG signals acquired, respectively, by electrodes 50 and 38. In case processor identifies IC and/or BS ECG signals, which are in the rhythm of the sinus node, the method continues to an IRE ablation step 106, which terminates the method.

At IRE ablation step 106, based on the IC and/or BS ECG signals that are in the rhythm of the sinus node, processor 41 is configured to: (i) detect a refractory period of the patient heart, and (ii) control IPG 45 to apply IRE pulses for ablating tissue at an ablation site of heart 26, during the detected refractory period. Note that the IRE pulses are applied to the tissue via one or more pairs of electrodes 50 selected by switching box 46 or using any other suitable selection mechanism.

Note that the method described in FIG. 2 is carried out automatically, e.g., without intervention of physician 30, however, physician 30 may have the means to intervene, and if needed, to adjust or abort the automatic IRE ablation procedure described above.

Although the embodiments described herein mainly address IRE ablation of cardiac tissue, the methods and systems described herein can also be used in other applications, such as in ablating other organs of humans or other mammals.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for performing irreversible electroporation during heart refractory period, the method comprising:
    inserting an ablation catheter into an ablation site in a patient heart;
    acquiring both body surface (BS) electrocardiogram (ECG) signals and intra-cardiac (IC) ECG signals;
    detecting, based on the acquired BS ECG signals, the acquired IC ECG signals, or both the acquired BS ECG signals and the acquired IC ECG signals, a sinus rhythm that is initiated naturally by a SA node of the patient heart;
    identifying a refractory period of the patient heart during the detected sinus rhythm;
    selectively activating a generator to deliver ablation energy to ablating the ablation site using the ablation catheter during the detected refractory period based on detecting the sinus rhythm.

2. The method according to claim 1, wherein ablating the ablation site comprises applying one or more irreversible electroporation (IRE) pulses to tissue at the ablation site during the detected refractory period.

3. The method of claim 1, wherein the detecting and the identifying is performed over an automated process without human intervention.

4. A system for performing irreversible electroporation during heart refractory period, the system comprising:
    a first one or more electrodes, which are configured to sense body surface (BS) electrocardiogram (ECG) signals of a patient heart and a second one or more electrodes, which are configured to sense intra-cardiac (IC) ECG signals; and
    a processor, which is configured, based on the acquired BS ECG signals, the acquired IC ECG signals, or both the acquired BS ECG signals and the acquired IC ECG signals, to detect a sinus rhythm that is initiated naturally by the SA node, identify a refractory period of the patient heart during the detected sinus rhythm, and is configured to control a generator to selectively activate ablation during the detected refractory period based on detecting the sinus rhythm.

5. The system according to claim 4, wherein the generator is an irreversible electroporation (IRE) pulse generator, which is configured to apply IRE pulses to tissue at the ablation site during the detected refractory period.

6. The system according to claim 5, wherein the generator is configured to apply one or more bipolar IRE pulses between selected one or more pairs of the second one or more electrodes.

7. The system according to claim 4, wherein at least one of the second one or more electrodes is fitted on a catheter and is configured to alternate between: (i) sensing intra-cardiac ECG signals at the ablation site, and (ii) applying one or more irreversible electroporation (IRE) pulses, to tissue at the ablation site.

8. A system for performing irreversible electroporation during heart refractory period, the system comprising:
    an interface, which is configured to receive both body surface (BS) electrocardiogram (ECG) signals of a patient heart and intra-cardiac (IC) ECG signals; and
    a processor, which is configured, based on the received BS ECG signals, the received IC ECG signals, or both the received BS ECG signals and the received IC ECG signals, to detect a sinus rhythm that is initiated naturally by the SA node, identify a refractory period of the patient heart during the detected sinus rhythm, and selectively activate a generator to deliver ablation energy during the detected refractory period based on detecting the sinus rhythm.

9. The system according to claim 8, and comprising an irreversible electroporation (IRE) pulse generator, which is configured to apply IRE pulses to tissue during the detected refractory period based on detecting the sinus rhythm.

* * * * *